United States Patent [19]

Abdallah

[11] Patent Number: 5,310,195
[45] Date of Patent: May 10, 1994

[54] BOARDGAME AND METHOD OF MEASURING BRAIN ACTIVITY UTILIZING A BOARD-GAME

[76] Inventor: Iman'al-Amin Abdallah, 33 Stanley Rd., South Orange, N.J. 07079-2721

[21] Appl. No.: 752,067

[22] Filed: Aug. 29, 1991

[51] Int. Cl.$^5$ ............................................. A63F 3/00
[52] U.S. Cl. ..................................... 273/444; 273/236
[58] Field of Search ................ 273/444, 236, 242, 261

[56] References Cited

U.S. PATENT DOCUMENTS 4,846,479 7/1989 Hanley .................................. 273/236

Primary Examiner—William H. Grieb
Attorney, Agent, or Firm—Abdallah & Muckelroy

[57] ABSTRACT

A boardgame apparatus and method of attenuating brain activity measurements by comparing representational systems for evoked responses generated while playing a game utilizing the boardgame apparatus resulting from stimuli of different form for the same change in brain state.

6 Claims, 4 Drawing Sheets

BOARDGAME AND METHOD OF MEASURING BRAIN ACTIVITY UTILIZING A BOARD-GAME

BACKGROUND OF THE INVENTION

The present invention generally relates to cybernetic engineering principles applied to the neurophysiological processes of the brain and in particular to a process for neurometric calibration and verification of brain cell-firing frequency patterns representing mental experience. More specifically, this invention discloses a method for attenuating brain activity measurements by comparing evoked responses from stimuli of different form representing the same progression of brain activity.

The process of the present invention is analogous to developing a historical record of a traffic accident by interviewing several witnesses who saw the accident from different perspectives. Thereby a more accurate picture of the events can be obtained through a synthesis of the varying viewpoints.

This invention is based in the antilocalizationist viewpoint of the mechanics of brain functioning. Brain activity is generally measured by EEG procedures. The value of EEG measurements is dependent upon analysis, and analysis is generally made by referencing static templates, i.e. patterns known to represent certain brain conditions. The present invention is a device and method for developing distinct measurable parameters for simultaneous trial of events, or a "dynamic template." Boardgames are used in the art as brain activity stimulators for brain activity measurements.

More recent evidence against the localization of brain function include the recording from a widespread extent of cortex, evoked potentials (Doty, 1958) or responses of single neurons (Burns, Heron, & Grafstein, 1960) to visual stimuli; the ability of visual discrimination after extensive ablations of cortical and collicular regions of the visual system (Urbaitis & Hinsey, 1966; Winans & Meikle, 1966); and among others, the ability for auditory frequency discrimination by cats after bilateral ablation of all cortical auditory areas resulting in complete retrograde degeneration of the medial geniculate body (Goldberg & Neff, 1964).

The initial phases of neuroscientific study concerned itself with investigations of sensory, motor, and reflex functions. More recently, increasing attention has been given to neural activity concerned with behavior. From these more recent investigations, a hypothesis of a centralized integrative system to represent the gross organization responsible for conscious activity has been developed. Consideration of the intrinsic properties of reticular arrangements of neurons with short axons has led to two important conclusions: (1) in reticular systems, the dynamic properties of neurons working en masse predominate over the consequences of activity of single cells; and (2) due to the shortness of most recticular axons, interactions of graduated somatodendritic potentials are more predominant in the control of activity in such systems than axonal spikes.

Information appears to be represented in the brain by the temporal pattern of nonrandomness, or organization, in the firing of ensembles of many neurons rather than by the activity of individual cells. At any moment, a particular anatomic distribution of such nonrandom activity patterns exists in the brain. From each of the various regions of the brain experiencing nonrandom activity, neural outflow propagates to other regions exerting influence which causes further nonrandom activity. The resulting interaction between patterns of organized neural discharge arising, interacting, and subsiding throughout the brain represents the instantaneous fluctuation of information in the system. The organized nature of the activity defines the activity as informational, the anatomic locus of the ensemble defines the modality of the information, and the details of the temporal pattern describe the content of the information.

The different informationally significant facets of momemtary experience is called the representational system for that experience. Similar electrical patterns have been observed in many different brain regions when a familiar event occurs, which reflects the functioning of the distributed anatomic network of the organized neuronal patterns. A representational system is any structure of which the features symbolize or correspond in some sense to some other structure (Mackey, 1969). Consciousness, itself a representational system, is a consequence of the occurence of a set of temporal sequences of nonrandom activity in a set of interacting anatomic structures. The modality of the facets of conscious experience, or form, depends upon the anatomic location of the neuronal ensembles in which the statistical processes emerge. The shape of the separate facets of conscious experience, or content, depends upon the temporal pattern of the nonrandom activity in each of these brain regions.

The prior art has not clearly determined whether or not the informational patterns which constitute the content of consciousness arise in some central integrative system receiving input from all other anatomic regions sustaining informational patterns or arise as a result of the interactions between the various regions. However, the prior art postulates that the content of consciousness is defined by the statistical features of activity in an anatomically diffuse network of neurons, although the precise physical nature of those consequences or the cooperative process which are responsible for consciousness are not understood.

Most recent work within the prior art has further developed certain basic ideas: (1) information in the nervous system is represented by the statistical behavior of neuronal ensembles rather than by the firing of any individual cell; (2) the constituent activities of the ensemble are postsynaptic potentials and axonal spikes, unitary events of transient electrical process, a shift in ionic concentrations and charge densities, which possess gestalt properties not contained in the individual parts; (3) mental experience arises from the cooperative behavior of neuronal ensembles; and (4) the physical properties of the neuronal ensemble processes which generate subjective experience as the result of cooperative behavior of neurons may relate to the ways in which energy is organized by neuronal masses, and may reflect general properties of matter (Thatcher & John, 1977).

The prior art has established that the representation of information within the brain, whether concrete information about the present or abstractions about such information, is organized and statistical in nature. Predictions from such statistical formulations are also supported by experiment. However, the prior art has not determined the processes of change from the organized activity of representational systems, a state of zero entropy, to the universal tendency toward chaos, or positive entropy, asserted by the laws of thermodynamics, and likewise the change processes from predetermined activity of the representational systems of information.

When a sensory stimulus is presented to a human subject, a transient oscillation of voltage occurs in the EEG recorded from electrodes over responsive brain regions, which often is obscured by other ongoing activity. This oscillation, or evoked response, represents the response of the brain to the sensory stimulus and occurs at a latency determined by the central transmission time of the sensory system that was stimulated. By use of an averaging technique, often implemented by a special-purpose average response computer, the details of the waveshape of the voltage oscillations that are time-locked to the delivery of the sensory stimulus can be ascertained from the average evoked response (AER). The visual, somatosensory, and auditory systems all involve a set of specialized peripheral receptors capable of transducing specific environmental energies into nerve impulses which are conducted in what are called "primary sensory" pathways to "relay stations" located in the thalamus. The waveshape of the AER reflects the anatomy of the responding systems, the characteristics of the stimulus, and certain dynamic factors. Averaging evoked responses improve the signal-to-noise ratio, or accuracy of definition of the evoked response, by an amount proportional to the square root of the number of samples obtained.

Since the advent of the average response computer, numerous investigators have discussed the characteristics of the AER in various types of neuropathology, and have drawn inferences about brain function based upon deviations of certain components of the waveshape from some expected normal contour. Such AER methods have won little acceptance in routine clinical practice, perhaps because of the AER waveshape dependence on visual recognition of patterns by the practitioner, a similar shortcoming of qualitative evaluation of the EEG. In order to achieve more precise, objective criteria for EEG diagnosis requires that impressionistic evaluation of the EEG be replaced by numbers and that subjective descriptions be replaced by mathematical characterizations.

The prior art has described a digital electrophysiological data acquisition and analysis system which permits the rapid, automatic acquisition of precise data about a spectrum of functionally significant electrophysiological measures and their reduction to numerical taxanomic classification of such data have also been surveyed. These endeavors have established the theoretical practicality of quantitative and objective evaluation of the combination of neurometric and numerical taxonomic methods. Background research has generally been directed toward use in diagnosis, treatment, and prognosis of diseases and brain dysfunction and the practical utility of these methods has been demonstrated through studies of normal and those suffering from neurological diseases; normal and learning disabled children. Methods for neurometric analysis of the EEG mostly have concerned themselves with objective determination of the frequency distribution, or spectral analysis. The differences in individual perception of a common stimuli necessitates means for calibration and verification of the brain cell-firing frequency pattern measurements.

Most electroencephalographers consider bilateral symmetry of waveform and amplitude an important feature of the EEG, sensitive to neuropathology. Symmetry measures place lower importance on the absolute frequency composition of the EEG signal, and rely more on the use of the EEG from one hemisphere as the "control" relative to the other. Symmetry values are usually comparable and correspond well to the symmetry of the overall EEG activity. Spontaneous EEG reflects ongoing electrical transactions between and within various anatomic regions of the brain related to its intrinsic organization. Evoked response provides insight into the reactivity of various functional systems of the brain to afferent input and tells something about how the system processes different kinds of information. Symmetry measures circumvent the issue of "normal morphology" of brain activity and the interindividual variability in spectral analysis.

Two methods for quantitative evaluation of AER symmetry are (1) cross-correlation between AERs derived simultaneously from bilaterally symmetric derivations and (2) significance of differences between bilateral pairs of AERs. The prior art also includes a symmetry analyzer which measures waveform symmetry based upon utilization of polarity coincidence correlation methods which consist of making a large number of comparisons of the polarity (positivity or negativity) of two simultaneous electrical signals, and measures amplitude symmetry by rectifying and integrating each input signal and computing the ratio of the integrated absolute amplitudes.

Pattern recognition methods include (1) template methods, (2) cluster analysis, (3) discriminant analysis, and (4) multi-dimensional scaling. Template methods employ data analysis procedures involving assumptions about the features of some particular event being sought or the general nature of the structure of the solution to some problem. This method can be viewed as a process of scanning a long train of samples of electrical waveshapes to identify recurrences of the template. Cross-correlation between the template and the train of samples of electrical waveshapes to identify recurrances of the template and using the shifting theorem and the cross-spectral theorem of Fourier analysis are techniques used to rectify measurements of this method. Another method is the adaptive filter method, an extension of the cross-spectral technique where the template is iteratively redefined. All template methods suffer from the constrain of someone specifying the basic characteristics of the process or event describing the template.

Cluster analysis is an analytic method that describes the details characterizing the structure of a body of data. Cluster analysis ascertains, given a set of feature vectors, how many groups are contained within that structure and which elements most probably belong to each group. This method offers the advantage over the template method in that it permits the structure of a body of data to be analyzed in the absence of prior assumptions about the nature of the structure. Nonetheless, some guidance must be provided.

Discriminant analysis can be conceptualized as a mapping of each feature vector into a multivariate space. This is a technique for finding an optimal vector, which minimizes the spread within distributions and maximizes the separation between the centroids or the two sets of points projected upon that vector, thus providing the best possible discrimination between the two bodies of data. Discriminant analysis ascertains, given a set of features characterizing two or several groups of data, which features best discriminate between the two groups and what are the clusters of feature vectors corresponding to the discrimination.

Multi-dimensional scaling is a graphic approach to cluster analysis. It is a method of mapping distances between data points. The original distances are in the (high-dimensional) space of the feature vector, and the distance function is the similarity measure; the final space is a two-(or three-) dimensional space of points with the property that the distances between these points are equal to the original distances. The distance function used in the final space is not necessarily the same as the similarity measure.

In order to make electrophysiological measurements more readily available and more precise, and to extend their utility into new areas of application, the following conditions must be met:

(1) optimal instrumentation must be devised to gather data in a standardized fashion and maximize the efficiency and accuracy of data processing;

(2) a set of *challenges* must be devised that reflect important aspects of brain function in particular electrophysiological measurements. There is no reason to expect that any stimulus delivered to the central nervous system will provide useful insights into the manner or adequacy with which some particular function is performed by the brain, unless the context of the situation in which the stimulus is imbedded, as well as the stimulus itself, is devised to exercise that particular capability; and (3) the essential features of each of these measures must be quantified, so that they can be represented numerically and manipulated statistically and mathematically.

A quantitative electrophysiological test battery (NB) has been developed in the prior art. Basic neurometric indices computed for each derivation under each condition defining an EEG measure in the NB include distribution of energy in different frequency bands, age-dependent quotient, energy ratios, energy symmetry, and waveform symmetry. The plausibility of each challenge comprising the NB has not been documented and is based upon findings of previous experiences.

The digital electrophysiological data acquisition and analysis system, and the quantitative electrophysiological test battery developed in the prior art are useless until normative data are acquired, and until systematic correlations are established between the indices of brain function which they provide and functional measures obtained by the conventional techniques of neurology and psychology. Techniques must also be devised to segregate the meaningful numbers (signal) from the meaningless numbers (noise). As well, a method of encompassing the vast body of data produced for an individual by a discrete set of descriptors must be devised. These descriptors must achieve a great deal of data compression for the present system of data acquisition, yielding profiles of deviation from expected or probable values for various functions which permit classes of individuals with similar etiologies to be identified.

DISCLOSURE OF INVENTION

An object of this invention is to provide a process for calibration and verification of measurements of the neuronal representational systems of conscious mental experience. Another object of this disclosure is to provide means for the determination of the precise physical nature of the consequences of the cooperative process which are responsible for thought progression.

Another object of this disclosure is to provide means for the establishment of the "normal" morphology of brain activity. A further object of this invention is to provide a method of brain activity pattern recognition which is independent of subjective specification of the basic characteristics. It is also an object of the disclosure of this invention to provide a set of challenges imbedded in a representational system which corresponds to the temporal sequences of nonrandom activity in the brain cell-firing frequency patterns of consciousness.

It is a further object of this invention to provide means for translating thought progression representational systems into musical notation. It is also an object of this invention to provide means for intuitive recognition as "control" for the attenuation of brain activity representational systems. Another object is to provide means for describing quantitatively the morphology of brain activity. A still further object of the invention of this disclosure is to provide a method of simplifying the representation of critical features of the electroencephalogram (EEG) for interpretation by non-electroencephalographers. It is also an object of this invention to provide means for development of the absolute frequency composition of the EEG signal across the whole brain through comparison of representational systems derived for different stimuli for the same change in brain state. It is also an object of this invention to provide means for attenuating the threshold value between preconscious and conscious experience.

Another object of this invention is to provide a device for the measurement of brain activity while engaged in competition. A further object is to provide a device for comparison of representational systems of a plurality of individuals within the same framework of mental experience.

It is also an object of this invention to provide an article of manufacture for mental execution of entropy reduction. It is still a further object to provide an article of manufacture for use in the translation of finger and thumb movements, or appropriate extensions or distinguishable representatives thereof, into musical sound notations.

It is a further object of this invention to disclose the threshold value of complexity for conscious mental experience.

The above and further objects of the invention are accomplished by means of a process of comparing the rate and method of change in the neuronal representational systems for averaged evoked responses to different stimuli for the same patterns of change in brain state. The mathematical basis for this process lies in recognizing the neuronal representational systems, nonradom states of brain cell-firing frequency patterns, as states of zero entropy. The process of this invention involves describing the change from nonrandom to random states of brain activity and the subsequent return to a nonrandom states. This process of change is required in order for sequential and different representational systems to arise in the continuum of mental experience. The plausibility of the process disclosed in this invention derives from the intimacy of the human hand and mind.

In one embodiment of the invention of this disclosure neuronal representational systems for somatosensory averaged evoked responses developed by movements of the fingers and thumb of the human hand within the spaces of the device of this disclosure, a circular disc with a pattern of four circular bands around a center circle, whereas, this pattern has been formed by turning in a counterclockwise direction into itself a basic musical staff, such staff being defined as five lines and four spaces, and whereas, the four circular bands thus formed have been further divided into eight equal parts, and each one-eighth section of the outermost circular band has been divided into two equal parts, are compared with the neuronal representational systems for auditory averaged evoked responses developed by the musical note patterns representing the same patterns of finger and thumb positions within spaces of the device of this invention. The fingers and thumb of the human hand are each represented by basic music symbols to denote pitch and duration. The neuronal representational systems for the averaged evoked responses are described by using the digital electrophysiological data acquisition and analysis system developed in the prior art (John, Neuronmetrics, 1977) or other suitable electroencephalogram analysis techniques.

The process of this invention provides a template method of pattern recognition employing the comparison of somatosensory and auditory averaged evoked responses, an improvement over the prior art, which depends upon the objective description of a template and subsequent scanning of electrical waveshapes to identify recurrences of the template.

The process of this invention includes the intuitive aspect of mental experience in the attenuation of neuronal representational systems by the development of brain activity measures in terms of musical sounds. The subjective nature of the subject upon whom the brain activity measurements are taken is used in the attenuation of the cell-firing frequency patterns. The power of music as an entity within itself has recently become more widely recognized. Since individuals are in effect the sum of all their experiences, including emotional, physical, intellectual, and social experiences, the effect of any musical experience can be expected to differ for each. The process of this invention allows for individual variability in brain activity measure to be held consistent through a series of stimuli.

The process of this invention is imbedded in the challenge of movement from nonrandom state of activity to a random state and to the subsequent return to a nonrandom state, a process which occurs during displacement of energy between successive brain cell-firing frequency patterns. Consciousness itself can be recognized as a challenge against the forces of unconscious existence and the competitive nature of being is further emphasized in the surfacing of human will. The identification and measure of the system involved in the change in states of zero entropy involves the commensurate interaction of the basic components of neuronal representational states and represents the state of change in general.

BEST MODE FOR CARRYING OUT THE INVENTION

Figure 1:
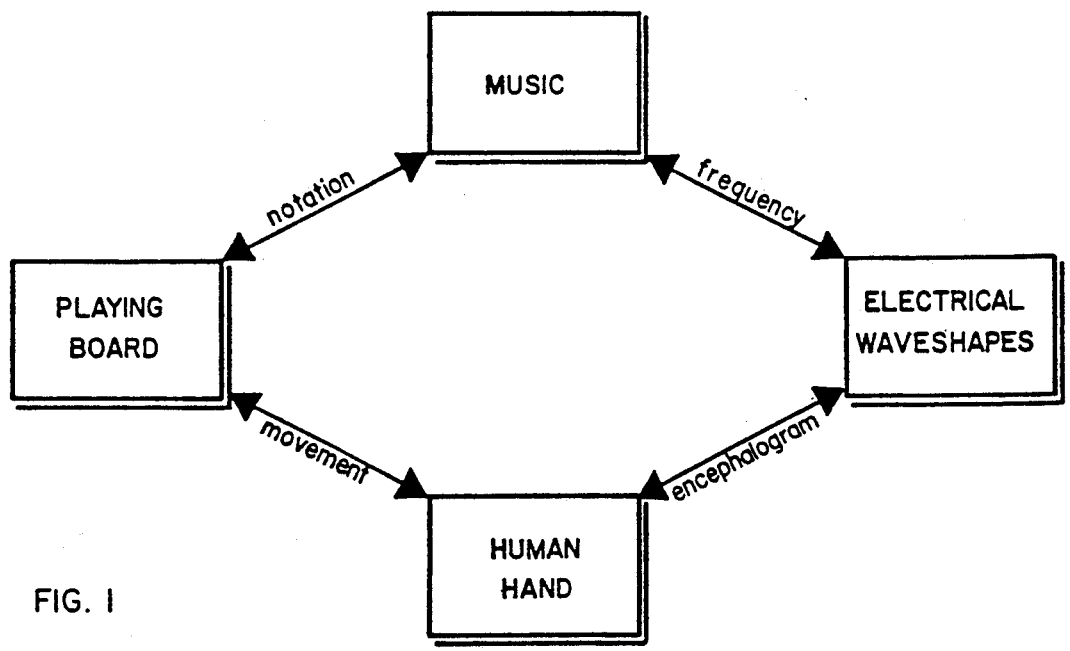
FIG. 1 is a diagram of the features of the process and the systems of comparison between these features in accordance with the teachings of this invention.
Figure 2:
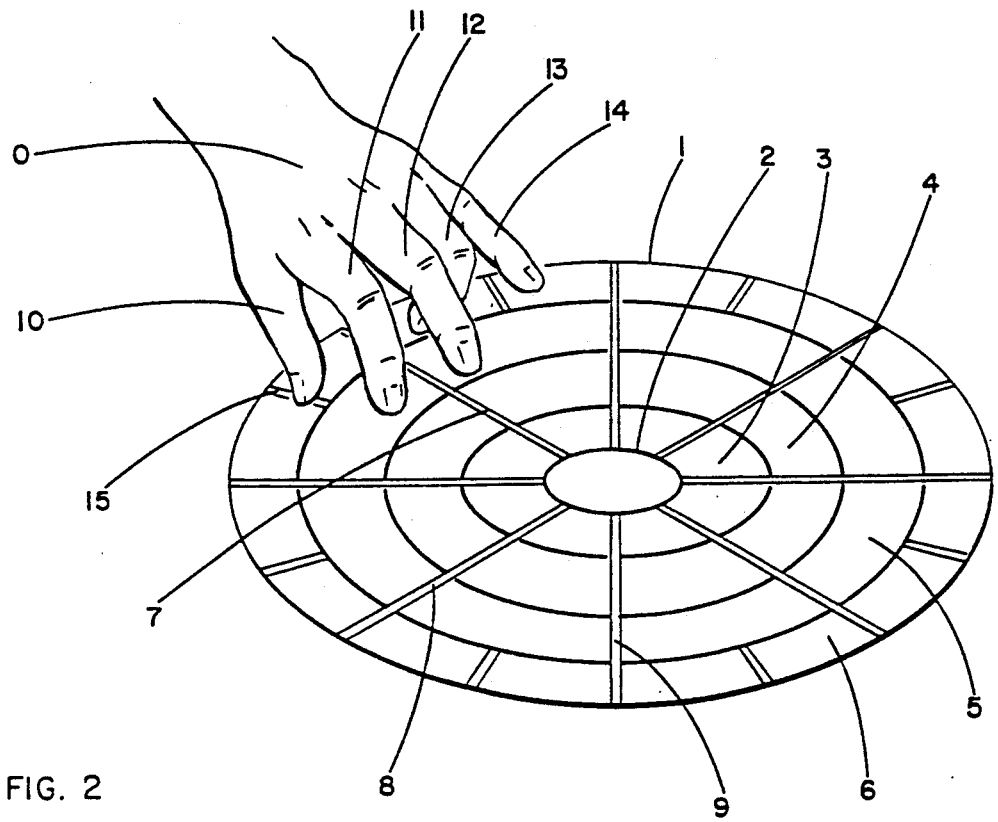
FIG. 2 is a perspective of the playing board device constructed in accordance with the teachings of this invention and the preferred initial positions of the finger and thumbs of the human hand upon the playing board device.

The features of the process of the invention (inside of the boxes) and the systems of comparison between these features are shown in FIG. 1. A preferred embodiment of the invention is shown in FIG. 2. The process of this invention involves the challenge of moving the fingers and thumb of the human hand (0) from their initial positions to the similar spaces on the opposite side of the playing board (1). The initial positions provide the potential energy that is exchanged in movement. The sequence of movements can be alternatively defined as movement from a zero entropy state to a positive entropy state to a subsequent return to a zero entropy state, which parallels the change in entropy between sequential nonrandom representational systems.

The playing board (1) of the disclosed invention is a two-sided circular disc comprising on each side four circular bands around a blackened center circle (2), whereas the four circular bands are divided into eight equal parts, and each one-eighth section of the outermost circular band (6) is further divided into two equal parts. On one side is a black and white schematic of the above-described pattern, and on the opposite side, each space of the innermost circular band (3) is the same shade of yellow, each space of the second innermost circular band (4) is the same shade of light blue, each space of the third innermost circular band (5) is the same shade of red, and the spaces of the outermost circular band (6) include paired light green spaces which are symmetrical about the vertical radials (7) relative to the initial position of the human hand (0), paired dark green spaces which are symmetrical about the horizontal radials (8), and orange and royal blue spaces symmetrical about the non-principal radials (9).

With the thumb (10) of the human hand (0) initially placed on the dividing line (15) of the one-eighth section of the outermost circular band (6), the index finger (11) of the human hand (0) placed in the space of the third innermost circular band (5), the middle finger (12) of the human hand (0) placed on the adjacent space of the third innermost circular band (5), the ring finger (13) of the human hand (0) placed in the right space of the two spaces of the outermost circular band (6) adjacent to the one-eighth section of the outermost circular band (6) where the thumb (10) is located, and the little finger (14) of the human hand (0) placed in the left space of the two spaces of the outermost circular band (6) adjacent to the one-eighth section of the outermost circular band (6) where the thumb (10) is located, movement of the human hand (0) is achieved by moving one, two, or more of the fingers and thumb of the human hand (0) either one space each along a radial direction or one space each around a circular band of the playing board (1); or by moving in a radial direction for the same number of spaces exactly two of the fingers and thumb of the human hand (0) which are located in the symmetrical spaces of the playing board (1) defined by the vertical radials (7) or the horizontal radials (8) relative to the initial position of the human hand (0), or by moving around circular bands for the same number of spaces exactly two of the fingers and thumb of the human hand (0) which are located in the adjacent or non-adjacent spaces within the same one-eighth section of the circular bands of the playing board (1). The thumb (10) of the human hand (0) may also be moved diagonally across a vertical radial (7), a horizontal radial (8) or a non-principal radial (9). Only one finger or thumb of the human hand (0) may occupy any space at the same time.

The electrical waveshapes for the neuronal representational systems for the somatosensory averaged evoked responses resulting from each movement of the human hand (0) can be determined by using the digital electrophysiological data acquisition and analysis system developed in the prior art, or by other suitable electroencephalogram analysis techniques. The digital electrophysiological data acquisition and analysis system is described in detail in the publication *Neurometrics*, E. Roy John, 1977.

The hand is considered to be the better genius of the microcosm of the human mind, the body's will and intellect, and the brother of desire. The gestures of the hand speak and show the mental springs from whence they naturally arise. Muscle, which controls the movement of the human hand (0), has a power of contraction and relaxation, termed irritability, which allows performance of various functions not reproducible, prior to this invention, by any or combinations of the properties that define our existence. The intimacy of the human hand (0) and the mind allows for definitive measure of the human will in terms of electrical waveshapes.

Figure 3:
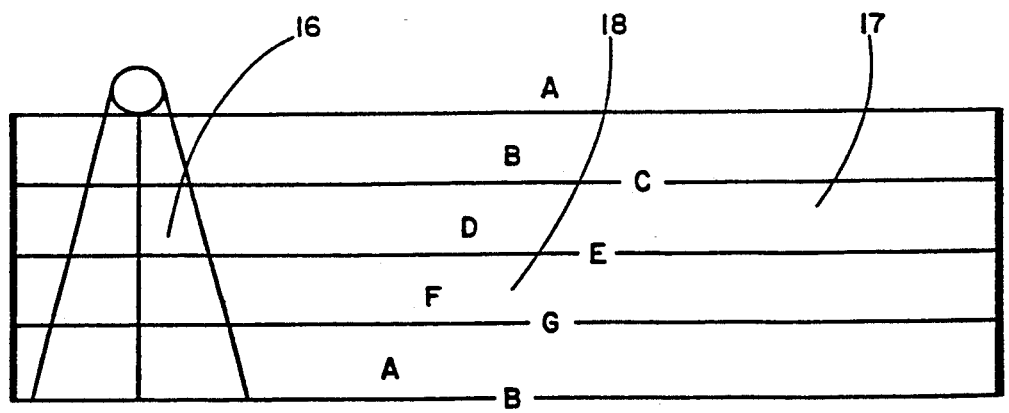
FIG. 3 is a preferred embodiment of the clef and musical staff for sound notation in accordance with the teachings of this invention.

Recognizing the basic pattern of four circular bands around a center circle that is described within the playing board (1) as a music staff consisting of five lines and four spaces turned in a counterclockwise direction into itself, provides the basis for translating the movements of the fingers and thumb of the human hand (0) into music notation. A preferred embodiment of the space clef (16) and staff (17) for representation of the movements of the fingers and thumb of the human hand (0) within the spaces of the playing board (1) is shown in FIG. 3. When a clef is placed on a music staff, a specific pitch (18) is assigned to each line and space of the staff. Similarly, a space clef (16) is used to determine the pitch for representation of the movements of the fingers and thumb of the human hand (0) within the spaces of the playing board (1) in accordance with the teachings of this invention.

Figure 4:
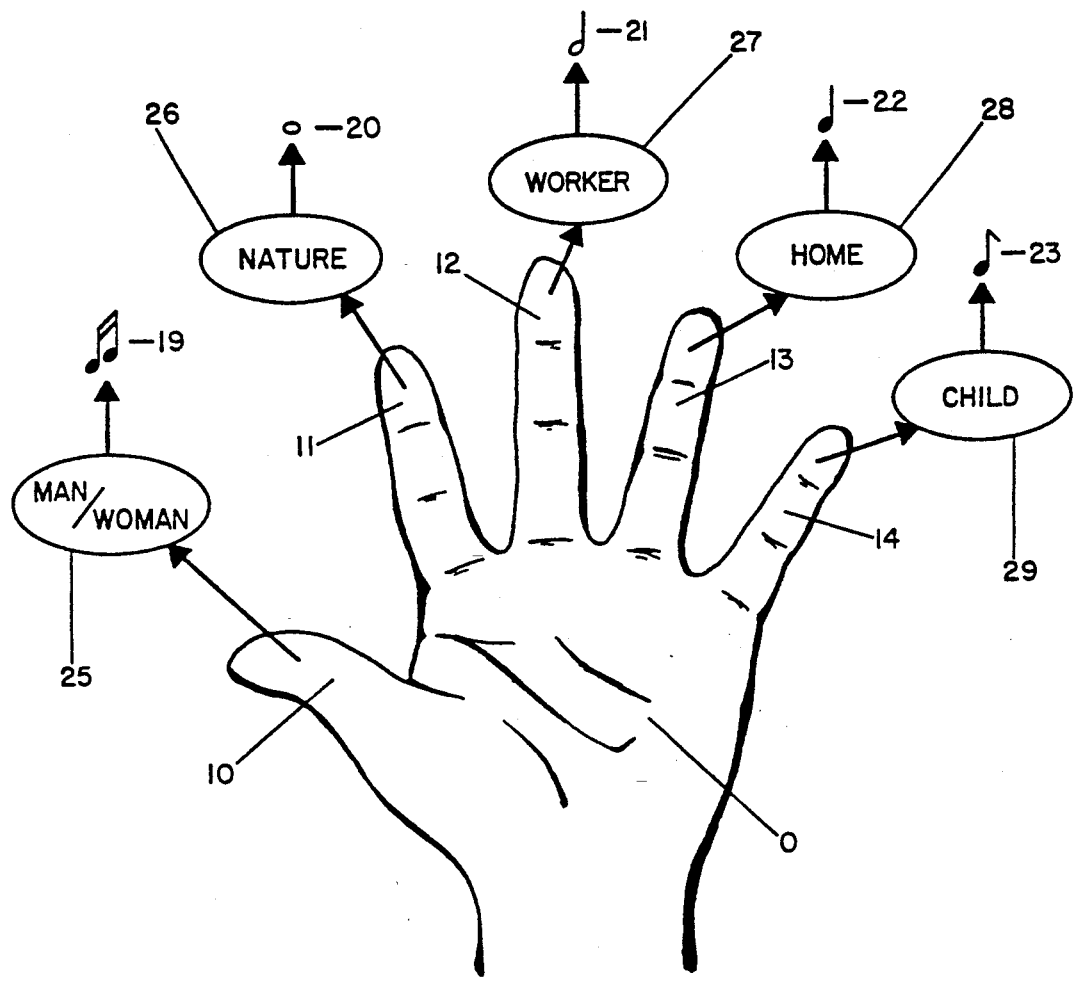
FIG. 4 is a diagram depicting musical notes as corresponding first distinguishable representations of the fingers and thumb of the human hand.

FIG. 4 is a diagram depicting the corresponding musical notes and distinguishable representations of the fingers and thumb of the human hand (0). Upon movement of the fingers and thumb of the human hand (0) in accordance with the teachings of this invention, a system of five symbols representing the duration of definable sounds, such sounds being a result of regular recurring vibrations, is placed on the staff (17) to represent the positions of the fingers and thumb of the human hand (0). The thumb (10) is represented by a pair of sixteenth notes, ♬ (19); the index finger (11) is represented by a whole note, 𝅝 (20); the middle finger (12) is represented by the half note, 𝅗𝅥 (21); the ring finger (13) is represented by the quater note, ♩ (22); and the little finger (14) is represented by the eighth note, ♪ (23). These notations for the fingers and thumb of the human hand (0) in combination are sufficient and complete for representation of two measures of music indicated by a four-four meter signature, with the notation for the index finger (11) completing one measure and the notation for the thumb (10), the middle finger (12), the ring finger (13), and the little finger (14) completing a second measure. The positions of the fingers and thumb of the human hand (0) within the center circle and the spaces of the half of the playing board (1) where the human hand (0) is initially located are noted in the corresponding spaces of the staff (17); the positions of the fingers and thumb of the human hand (0) within the spaces of the opposite half of the playing board (1) are noted on the corresponding lines of the staff (17).

The electrical waveshapes for the neuronal representational systems for the auditory average evoked responses resulting from the musical sounds representing each movement of the human hand (0) can be determined by using the digital electrophysiological data acquisition and analysis system developed in the prior art, or by other suitable electroencephalogram analysis techniques. The digital electrophysiological data acquisition and analysis system is described in detail in the publication *Neurometrics*, E. Roy John, 1977.

Throughout the ages the therapeutic value of music has been recognized and respected. It is mentioned in the early writings of the Chinese, Greeks, Africans, Persians and Hindus. Our bodies have a pulse, and so does music. In a healthy state, we are in touch with our "inner pulse". The inner pulse represents a certain point of view. The phenomenon of the inner pulse is in effect an internally conducted beat. Because of the intimacy of music and the mind, it is possible for humans to appreciate fully the effects of a series of chords without knowing the technical names of the progressions. Music, being a result of regular recurring sound vibrations, can be reduced to patterns of frequencies which allows a definitive comparison to the cell-firing frequency patterns of brain activity.

Figure 5:
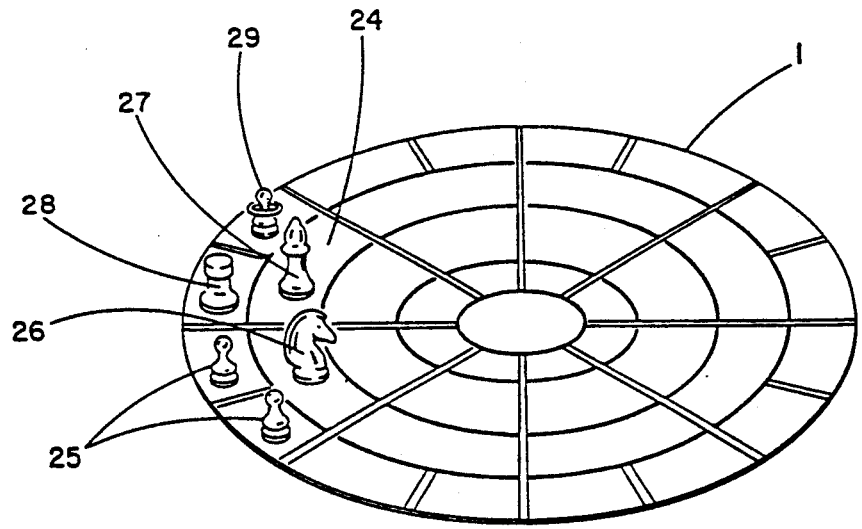
FIG. 5 is a perspective of the playing board device constructed in accordance with the teachings of this invention and second boardgame playing pieces as corresponding distinguishable representations of the fingers and thumb of the human hand.

A further embodiment of the disclosed invention is shown in FIG. 5. This embodiment of the invention comprises a playing board (1) and distinguishable representations of the fingers and thumb of the human hand (0) within a social perspective. These distinguishable representations of the fingers and thumb of the human hand (0) are called a Family (24). The members of a Family (24) correspond to the fingers and thumb of the human hand (0) as follows: the thumb (10), Man/Woman (25); the index finger (11), Nature (26); the middle finger (12), Worker (27); the ring finger (13), Home (28); the little finger (14), Child (29).

The process of the disclosed invention is performed in the same manner using the distinguishable representations of the fingers and thumb of the human hand (0), but their use is contingent upon the satisfactory correlation of the movements of the fingers and thumb of the human hand (0) and the resulting somatosensory average evoked responses of brain activity.

The process for attenuation of the waveshapes of neuronal representational systems as disclosed in this invention involves a device for comparison of somatosensory and auditory average evoked responses of brain activity. To rectify the utility of this device, a series of challenges are included in the disclosure of this invention which may eventually be displaced by more sensitive measures, but provide the basis for attenuation of the utility of the playing board (1) device disclosed in this invention.

Condition 1: Spontaneous EEG recording is obtained while the subject sits comfortably with eyes open, free to examine the recording chamber. Analysis of these data yields a number of measures of the transactions between various cortical and subcortical regions of the brain.

Condition 2: Spontaneous EEG recording is obtained while the subject sits comfortably with eyes closed and room lights off. Analysis of these data yields measures of the transactions between cortical and subcortical regions while the subject receives decreased afferent input.

Comparison of Conditions 1 and 2 constitutes Challenge 1, an important measure of reactivity, the changes in intrinsic activity caused by removal of visual afferent input.

Condition 3: Stimulated evoked response recording is obtained while the subject looks at a blackened circle as contained in the center of the playing board. This condition defines Challenge 2, which constitutes an additional measure of reactivity, the visual perception of a circular shape.

Condition 4: Stimulated evoked response recording is obtained while the subject views a black and white schematic diagram of the pattern of the playing board.

Comparison of Conditions 3 and 4 constitutes Challenge 3, the visual perception of space division within a circular shape.

Condition 5: Stimulated evoked response recording is obtained while the subject views a playing board with color patterns in accordance with the teachings of the invention of this disclosure.

Comparison of Conditions 4 and 5 constitutes Challenge 4, the visual color perception of space division within a circular shape.

Condition 6: Stimulated evoked response recording is obtained while the subject places the fingers and thumb of the human hand within the spaces of the playing board in accordance with the teachings of the invention of this disclosure. This condition defines Challenge 5, the habituation to a somatosensory stimuli, reflected in the features of the average evoked response.

Figure 6:
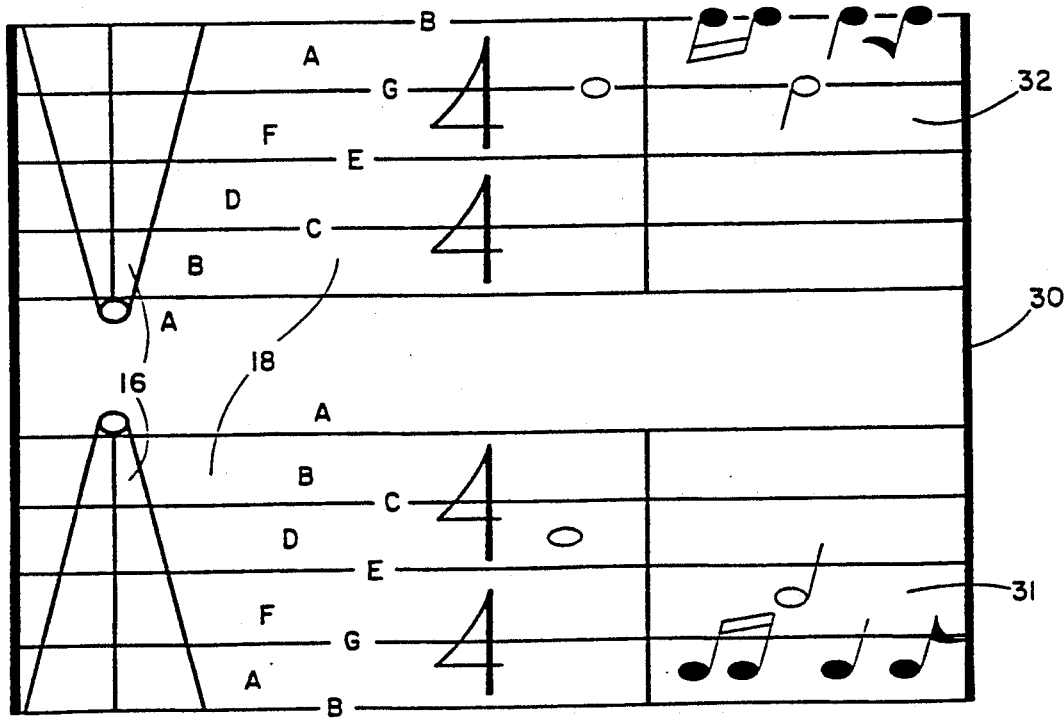
FIG. 6 is an embodiment of the musical score sheet for sound notation in accordance with the teachings of this invention.

The process and device of the invention of this disclosure can be employed in measuring the brain activity in a competitive perspective by developing electrical waveshapes for two or four subjects involved in movement from mutually opposite spaces of the playing board (1). The musical notation for two players or a plurality of pairs is scored on a grand staff (30) in accordance with the teachings of this invention. A preferred embodiment of this grand staff (30) is shown in FIG. 6. The movement of the player making the initial movement is noted on the bottom staff (31) of the grand staff (30) and the movement of the opposite player is noted on the top staff (32) of the grand staff (30). The movements of four players are noted on quadruple staffs, or double grand staffs (30). The specific pitch (18) representation of the space clef (16) in the preferred embodiment and music notation for initial positions of the fingers and thumb of the human hand for two players in accordance with the teachings of this invention is also shown in FIG. 6.

Figure 7:
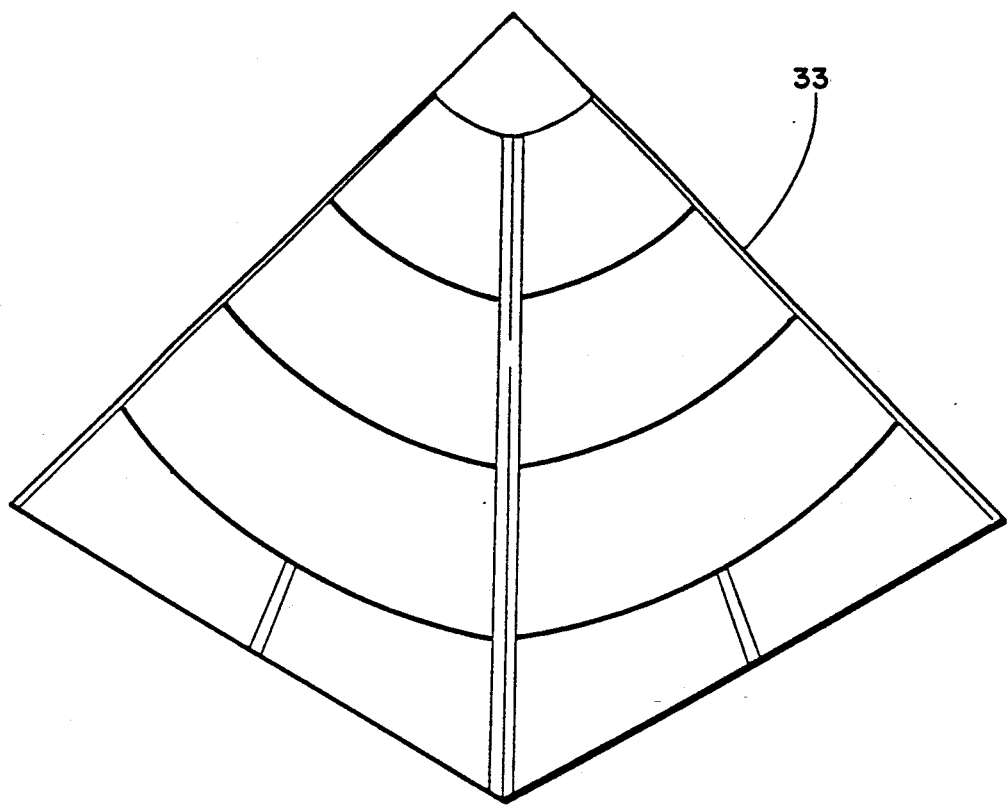
FIG. 7 is a preferred embodiment of the playing board device constructed in accordance with the teachings of this invention.

Another preferred embodiment of the playing board device (33), as shown in FIG. 7, comprises a pyramid with the space and color divisions of one-half of the circular playing board (1).

In summary of the foregoing description, a process for attenuation of the cell-firing frequency patterns of brain activity has been presented which involves the comparison of electrical waveshapes for somatosensory evoked responses and auditory evoked responses representing the same change in brain state. By providing means for the movement of the fingers and thumb of the human hand from a nonrandom to a random to a subsequent nonrandom state, a system which parallels the change in nonrandom states of neuronal representational systems is described. The described process provides means for measuring the rate of change in mind and brain interaction. Man does not possess a unique "divine spark" which confers subjective experience, but rather man may experience the divine nature of existence upon the assimilation in perfect harmony of a dynamic state in zero entropy.

While particular embodiments of this invention have been shown and described, it will be understood by those skilled in the art that various changes and modifications in the form and colors of the playing board and music notation pitch relationships may be made without departing from this invention in its broader aspects and it is therefore aimed in the appended claims to cover all such changes and modifications as fall within the spirit and scope of this invention.

Therefore, in view of the foregoing, I claim:

1. A boardgame apparatus for stimulating brain activity during EEG measurements, said boardgame apparatus comprising
   a playing board comprising a circular disc having a playing surface disposed on one side of the circular disc, said playing surface consisting of a plurality of playing spaces formed by four circular bands concentrically disposed about a center space, each of said four circular bands being divided into eight parts by radials extending from the center space, each one-eighth part of the outermost circular band being further divided into two parts.

2. A boardgame apparatus as in claim 1 wherein each part of the innermost circular band is the same shade of yellow, each part of the second innermost circular band is the same shade of light blue, each part of the third innermost circular band is the same shade of red, and the parts of the outermost circular band include paired light green parts which are symmetrical about opposing radials, paired dark green parts which are symmetrical about radials disposed at 90-degrees from the radials marking the paired light green parts, and orange and royal blue parts symmetrical about the remaining radials.

3. A boardgame apparatus as in claim 1 further including five distinguishable representations of human fingers and thumb.

4. A method of measuring brain activity utilizing the boardgame apparatus of claim 3 comprising
   moving the fingers and thumb of a human hand in the parts of the playing surface of the playing board,
   recording somatosensory averaged evoked responses corresponding to said movement of the fingers and thumb,
   translating said movement of the fingers and thumb into musical notation,
   producing musical sounds corresponding to said musical notation, recording auditory averaged evoked responses corresponding to said musical sounds, comparing said somatosensory averaged evoked responses and said auditory averaged evoked responses.

5. A method of measuring brain activity utilizing the boardgame apparatus of claim 2 comprising moving the fingers and thumb of a human hand in the parts of the parts of the playing surface of the playing board, recording somatosensory averaged evoked responses corresponding to said movement of the fingers and thumb, translating said movement of the fingers and thumb into musical notation, producing musical sounds corresponding to said musical notation, recording auditory averaged evoked responses corresponding to said musical sounds, comparing said somatosensory averaged evoked responses and said auditory averaged evoked responses.

6. A method of measuring brain activity utilizing a boardgame apparatus comprising developing a first physical representational system for evoked responses resulting from a first stimuli of a first form, developing a second physical representational system for evoked responses resulting from a second stimuli of a second form, said first stimuli and said second stimuli representing a same change in brain state, comparing said first representational system and said second representational system to attenuate a brain activity measurement.

* * * * *